United States Patent
Tumer et al.

[19]

[11] Patent Number: 6,135,965
[45] Date of Patent: *Oct. 24, 2000

[54] SPECTROSCOPIC DETECTION OF CERVICAL PRE-CANCER USING RADIAL BASIS FUNCTION NETWORKS

[75] Inventors: Kagan Tumer, Sunnyvale, Calif.; Nirmala Ramanujam, Philadelphia, Pa.; Rebecca Richards-Kortum; Joydeep Ghosh, both of Austin, Tex.

[73] Assignee: Board of Regents, The University of Texas System, Austin, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/757,116

[22] Filed: Dec. 2, 1996

[51] Int. Cl.$^7$ .................................................. A61B 6/00
[52] U.S. Cl. ............................ 600/476; 600/408; 128/925
[58] Field of Search ................................... 600/407, 408, 600/473, 475, 476, 477, 478, 310, 342; 395/21, 924; 436/63, 64, 813; 250/461.2; 128/925

[56] References Cited

U.S. PATENT DOCUMENTS

| Re. 30,712 | 8/1981 | Macemon | 356/318 |
|---|---|---|---|
| 3,647,299 | 3/1972 | Lavallee | 356/41 |
| 3,789,832 | 2/1974 | Damadian | 128/2 R |
| 4,037,961 | 7/1977 | Macemon | 356/85 |
| 4,170,987 | 10/1979 | Anselmo et al. | 128/665 |
| 4,213,462 | 7/1980 | Sato | 128/634 |
| 4,479,499 | 10/1984 | Alfano | 128/665 |
| 4,569,354 | 2/1986 | Shapiro et al. | 128/665 |
| 4,637,400 | 1/1987 | Marcus | 128/653 |
| 4,718,417 | 1/1988 | Kittrell et al. | 128/303.1 |

(List continued on next page.)

FOREIGN PATENT DOCUMENTS

| 2042075 | 11/1982 | Canada | A61B 1/00 |
|---|---|---|---|
| 0604931 A2 | 7/1994 | European Pat. Off. | A61N 5/06 |
| 19631355 A1 | 2/1997 | Germany | A61B 1/04 |
| 2125986 | 3/1984 | United Kingdom | A61B 17/32 |
| WO 96/28084 | 9/1996 | WIPO | A61B 5/00 |

*Primary Examiner*—Marvin M. Lateef
*Assistant Examiner*—Shawna J. Shaw
*Attorney, Agent, or Firm*—Fish & Richardson P.C.

[57] ABSTRACT

An apparatus and methods for spectroscopic detection of tissue abnormality, particularly precancerous cervical tissue, using neural networks to analyze in vivo measurements of fluorescence spectra. The invention excites fluorescence intensity spectra in both normal and abnormal tissue. This fluorescence spectroscopy data is used to train a group (ensemble) of neural networks, preferably radial basis function (RBF) neural networks. Once trained, fluorescence spectroscopy data from unknown tissue samples is classified by the trained neural networks. This process is used to differentiate pre-cancers from normal tissues, and can also be used to differentiate high grade pre-cancers from low grade pre-cancers. One embodiment of the invention is able to distinguish pre-cancerous tissue from both normal squamous tissue (NS) and normal columnar (NC) tissue in a single-stage of analysis. The invention demonstrates significantly smaller variability in classification accuracy, resulting in more reliable classification, with superior sensitivity. Moreover, the single-stage embodiment of the invention simplifies the decision-making process as compared to a two-stage embodiment.

46 Claims, 10 Drawing Sheets

U.S. PATENT DOCUMENTS

| | | | |
|---|---|---|---|
| 4,930,516 | 6/1990 | Alafano et al. | 128/665 |
| 5,125,404 | 6/1992 | Kittrell et al. | 128/634 |
| 5,201,318 | 4/1993 | Rava et al. | 125/665 |
| 5,301,681 | 4/1994 | DeBan et al. . | |
| 5,331,550 | 7/1994 | Stafford et al. . | |
| 5,345,941 | 9/1994 | Rava et al. | 128/655 |
| 5,421,337 | 6/1995 | Richards-Kortum et al. . | |
| 5,421,339 | 6/1995 | Ramanujam et al. . | |
| 5,450,527 | 9/1995 | Wang . | |
| 5,485,530 | 1/1996 | Lakowicz et al. | 382/191 |
| 5,486,999 | 1/1996 | Mebane . | |
| 5,528,046 | 6/1996 | Ishikawa | 250/461.25 |
| 5,528,368 | 6/1996 | Lewis et al. | 356/346 |
| 5,539,517 | 7/1996 | Cabib et al. | 356/346 |
| 5,544,650 | 8/1996 | Boon et al. . | |
| 5,596,992 | 1/1997 | Haaland et al. . | |
| 5,599,717 | 2/1997 | Vo-Dinh | 436/63 |
| 5,612,540 | 3/1997 | Richards-Kortum et al. . | |
| 5,623,932 | 4/1997 | Ramanumjam et al . | |
| 5,657,362 | 8/1997 | Giger et al. . | |
| 5,660,181 | 8/1997 | Ho et al. | 128/665 |
| 5,664,574 | 9/1997 | Chance | 128/664 |
| 5,669,795 | 9/1997 | Richards-Kortum et al. . | |
| 5,687,716 | 11/1997 | Kaufmann et al. . | |
| 5,697,373 | 12/1997 | Richards-Kortum et al. . | |
| 5,701,902 | 12/1997 | Vari et al. . | |
| 5,741,648 | 4/1998 | Hemstreet, III et al. . | |
| 5,784,162 | 7/1998 | Cabib et al. . | |

SPECTROSCOPIC DETECTION OF CERVICAL PRE-CANCER USING RADIAL BASIS FUNCTION NETWORKS

BACKGROUND OF INVENTION

1. Field of the Invention

The invention relates to methods and apparatus used for the diagnosis of tissue abnormalities, and more particularly to detection of cervical tissue abnormalities by analysis of spectroscopic data.

2. Description of Related Art

Among the many forms of cancer, cervical cancer is the second most common malignancy in women worldwide, exceeded only by breast cancer. In the United States, cervical cancer is the third most common neoplasm of the female genital tract. In 1994, 15,000 new cases of invasive cervical cancer and 55,000 cases of carcinoma in situ (CIS) were reported in the U.S. In the same year, an estimated 4,600 deaths occurred in the United States alone from cervical cancer. Recently, the incidence of pre-invasive squamous carcinoma of the cervix has risen dramatically, especially among young women. Women under the age of 35 years account for up to 24.5% of patients with invasive cervical cancer, and the incidence is continuing to increase for women in this age group. It has been estimated that the mortality of cervical cancer may rise by 20% in the next decade unless further improvements are made in detection techniques.

Early detection of cervical cancer, or of the pre-cancerous state called squamous intraepithelial lesion (SIL), can reduce the mortality associated with this disease. Currently, a Pap smear is used to screen for CIS and cervical cancer in the general female population. In a Pap smear, a large number of cells, obtained by scraping the cervical epithelium, are smeared onto a slide, which is then fixed and stained for cytologic examination. The Pap smear is unable to achieve a concurrently high sensitivity and high specificity due to both sampling and reading errors. For example, estimates of the sensitivity and specificity of Pap smears screening have ranged from 11–99% and 14–97%, respectively. (As used herein, sensitivity is defined as the correct classification percentage on pre-cancerous tissue samples, and specificity is defined as the correct classification percentage on normal tissue samples.)

Furthermore, reading Pap smears is extremely labor intensive and requires highly trained professionals. A patient with an abnormal Pap smear indicating the presence of SIL is followed up by a diagnostic procedure called colposcopy, which involves colposcopic examination, biopsy and histologic confirmation of the clinical diagnosis. Colposcopy requires extensive training and its accuracy for diagnosis is variable and limited, even in expert hands. Moreover, diagnosis is not immediate. Thus, it would be desirable to provide a way to reduce cervical cancer rates by improving the methods for early detection. It also would be desirable to provide a diagnostic method that could improve the level of specificity and sensitivity, reduce the required skill level of the practitioner interpreting the results, and shorten the time that it takes to arrive at a diagnosis.

In vivo fluorescence spectroscopy is a technique which has the capability to quickly, non-invasively and quantitatively probe the biochemical and morphological changes that occur as tissue becomes neoplastic. The measured spectral information can be correlated to tissue histopathology to develop clinically effective screening and diagnostic techniques. By using automated data analysis techniques, there is the potential for an automated, fast, non-invasive and accurate pre-cancer screening and diagnosis system that can be used by non-experts.

Screening and diagnostic techniques for human cervical pre-cancer based on laser induced fluorescence spectroscopy have been developed recently; see, for example, U.S. patent application Ser. No. 08/403,446, which is incorporated by reference. In the '446 patent application, screening and diagnosis was achieved using a technique based on a multivariate statistical algorithm (MSA). This technique used principal component analysis and logistic discrimination of tissue spectra acquired in vivo. A variation of the MSA technique is also disclosed in N. Ramanujam et al., "*Development of a Multivariate Statistical Algorithm to Analyze Human Cervical Tissue Fluorescence Spectra Acquired* In vivo, Lasers in Surgery and Medicine 19:46–62 (1996), which is incorporated by reference.

The approach based on MSA consists of the following steps: (1) pre-processing to reduce inter-patient and intra-patient variation of spectra from a tissue type; (2) partitioning of the pre-processed spectral data from all patients into calibration and prediction sets; (3) dimension reduction of the pre-processed tissue spectra using principal component analysis (PCA); (4) selection of diagnostically relevant principal components; (5) development of a probability-based classification algorithm based on logistic discrimination; and (6) a retrospective evaluation of the algorithm's performance on a calibration set and a prospective evaluation of the algorithm's performance on the prediction set, respectively.

In the MSA approach, discrimination between SILs and the two normal tissue types requires two stages. Such discrimination is difficult because the two normal fluorescence intensity spectra lie above and below the SIL spectra, as shown in FIG. 1. Therefore, the MSA technique used two constituent processes: (1) a first stage to discriminate between SILs and normal squamous (NS) tissues, and (2) a second stage to discriminate between SILs and normal columnar (NC) tissues. However, this two-stage approach complicates the data collection and the decision-making processes.

Another technique for the diagnosis of cervical pre-cancer is disclosed in U.S. Pat. No. 5,421,339, which is incorporated by reference. That method relies on an analysis of slopes of the fluorescence spectra to diagnose diseased tissue.

The inventors have determined that it would be desirable to provide a technique for the spectroscopic detection of cervical pre-cancer that provides greater sensitivity and selectivity than prior techniques. Further, it would be desirable to provide such a technique which is quantitative and has little variation in accuracy. The present invention provides such a technique.

SUMMARY OF THE INVENTION

The invention is directed to an apparatus and methods for spectroscopic detection of tissue abnormality, particularly precancerous cervical tissue, using neural networks to analyze in vivo measurements of fluorescence spectra. The invention excites fluorescence intensity spectra in both normal and abnormal tissue. This fluorescence spectroscopy data is used to train a group (ensemble) of neural networks, preferably radial basis function (RBF) neural networks. Once trained, fluorescence spectroscopy data from unknown tissue samples is classified by the trained neural networks. This process is used to differentiate pre-cancers from normal tissues, and can also be used to differentiate high grade pre-cancers from low grade pre-cancers. One embodiment of the invention is able to distinguish pre-cancerous tissue from both normal squamous tissue (NS) and normal columnar (NC) tissue in a single-stage of analysis.

The invention demonstrates significantly smaller variability in classification accuracy, resulting in more reliable classification, with superior sensitivity. Moreover, the single-stage embodiment of the invention simplifies the decision-making process as compared to a two-stage embodiment.

The apparatus of the invention includes a controllable illumination device for emitting a plurality of electromagnetic radiation wavelengths selected to cause a tissue sample to produce a fluorescence intensity spectra indicative of tissue abnormality; an optical system for applying the plurality of radiation wavelengths to a tissue sample; a detecting device for detecting fluorescence intensity spectra emitted by the tissue sample as a result of illumination by the plurality of electromagnetic radiation wavelengths; and a neural network-based data processor connected to the detecting device for analyzing detected fluorescence spectra to calculate a probability that the tissue sample is abnormal.

The details of the preferred embodiment of the invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings refer to like elements.

DETAILED DESCRIPTION OF THE INVENTION

Throughout this description, the preferred embodiment in the examples shown should be considered as exemplars, rather than as limitations on the invention.

Basic Diagnostic Setup

To illustrate the advantages of the invention, fluorescence spectra were collected in vivo at colposcopy from patients. A portable fiber-optic laser fluorimeter was utilized to measure fluorescence spectra from the cervix in vivo. The excitation wavelengths for one study were 337 nm, 380 nm, and 460 nm. Rhodamine 6G (2 mg/l) was used as a standard to calibrate for day-to-day variations in the detector throughput. The spectra were background subtracted and normalized to the peak intensity of rhodamine. The spectra were also calibrated for the wavelength dependence of the system.

Tissue biopsies were obtained only from abnormal sites identified by colposcopy and subsequently analyzed by the inventive system in order to comply with routine patient care procedure. Hematoxylin and eosin stained sections of each biopsy specimen were evaluated by a panel of four board certified pathologists and a consensus diagnosis was established using the Bethesda classification system. In cervical tissue, non-acetowhite epithelium is considered normal, whereas acetowhite epithelium and the presence of vascular atypias (such as punctuation, mosaicism, and atypical vessels) are considered abnormal. Samples were classified as normal squamous (NS), normal columnar (NC), low grade (LG) SIL, and high grade (HG) SIL, and divided into training (calibration) and test sets, as shown in Table 1. To be useful, a clinical method must discriminate SILs from the normal tissue types.

TABLE 1

| Histo-pathology | Training Set | Test Set |
| --- | --- | --- |
| Normal | 107 (NS; 94; NC: 13) | 108 (NS: 94; NC: 14) |
| SIL | 58 (LG: 23; HG: 35) | 59 (LG: 24; HG: 35) |

Figure 1:
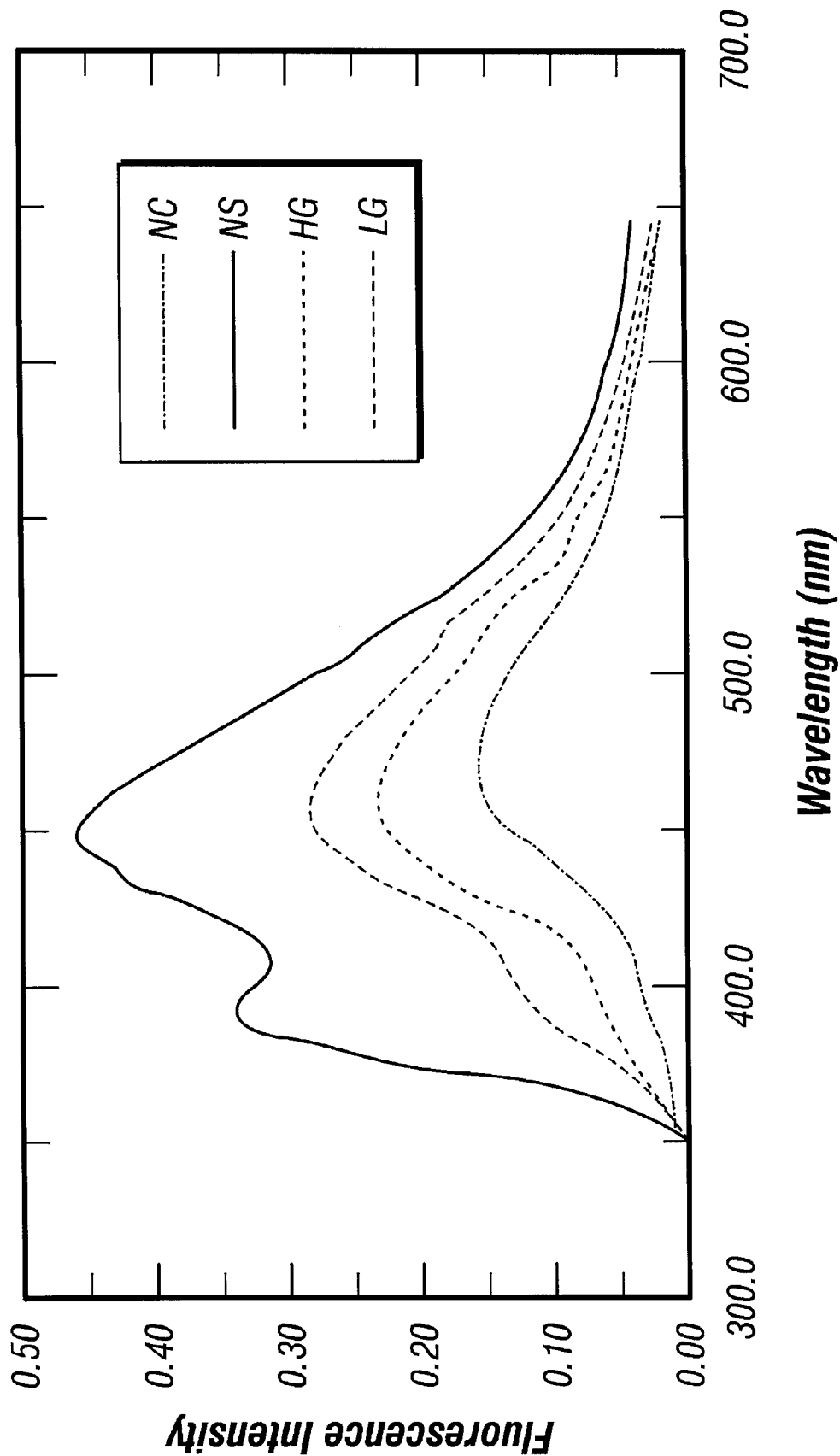
FIG. 1 is a fluorescence intensity spectra from a typical patient at 337 nm excitation.

FIG. 1 illustrates average fluorescence spectra per site acquired from cervical sites at 337 nm excitation from a typical patient. Evaluation of the spectra at 337 nm excitation highlights one of the classification difficulties: the fluorescence intensity of SILs (LG and HG) is less than that of the corresponding normal squamous tissue but greater than that of the corresponding normal columnar tissue over the entire emission spectrum.

Details of Diagnostic Apparatus

Figure 2:
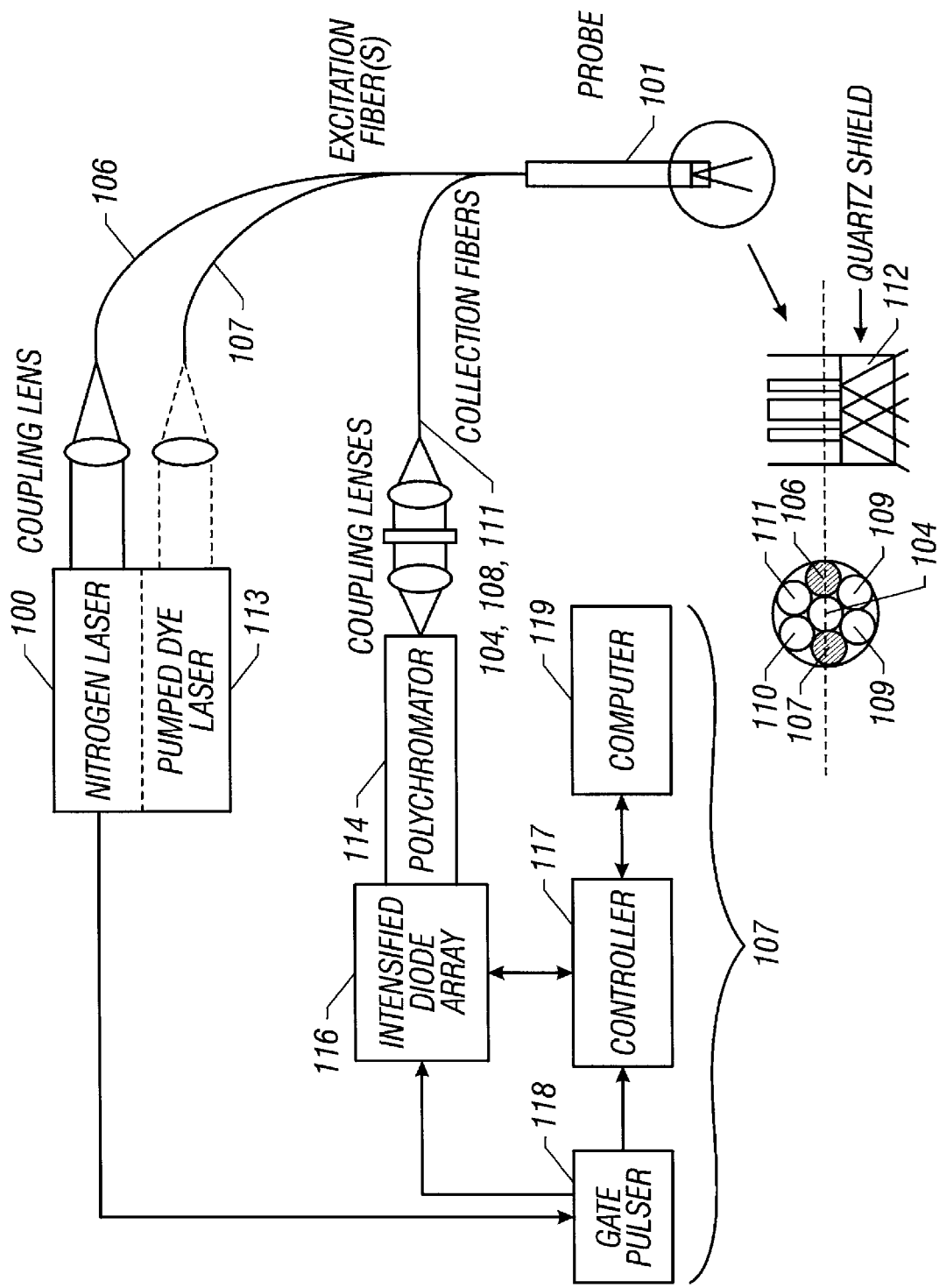
FIG. 2 is a block diagram of an exemplary fluorescence spectroscopy diagnostic apparatus in accordance with the invention.

FIG. 2 shows more details of an exemplary spectroscopic system for collecting and analyzing fluorescence spectra from cervical tissue, in accordance with the invention. This system includes a pulsed nitrogen pumped dye laser 100, an optical fiber probe 101, and an optical multi-channel analyzer 103 utilized to record fluorescence spectra from the intact cervix at colposcopy. The in vivo fiber-optic probe 101 comprises a central fiber 104 surrounded by a circular array of six fibers. All seven fibers have the same characteristics (0.22 NA, 200 micron core diameter). Two of the peripheral fibers, 106 and 107, deliver excitation light to the tissue surface. Fiber 106 delivers excitation light from the nitrogen laser. Fiber 107 delivers light from the laser dye module 113. Overlap of the illumination area viewed by both optical fibers 106, 107 is greater than 85%. The purpose of the remaining five fibers (104 and 108–111) is to collect emitted fluorescence from the tissue surface illuminated by the excitation fibers 106, 107. A quartz shield 112 is placed at the tip of the probe 101 to provide a substantially fixed distance between the fibers and the tissue surface, so fluorescence intensity can be reported in calibrated units.

Excitation light at 337 nm excitation was focused into the proximal end of excitation fiber 106 to produce a small (about 1 mm diameter) spot at the outer face of the shield 112. Excitation light from the laser dye module 113, coupled into excitation fiber 107, was produced by using appropriate fluorescence dyes. In this embodiment, BBQ (1E-03M in 7 parts toluene and 3 parts ethanol) was used to generate light at 380 nm excitation, and Coumarin 460 (1E-02 M in ethanol) was used to generate light at 460 nm excitation. The average transmitted pulse energies at 337 nm, 380 nm, and 460 nm excitation were 20 mJ, 12 mJ, and 25 mJ, respectively. The laser characteristics for this embodiment are: a 5 ns pulse duration and a repetition rate of 30 Hz; however, other parameter values would also be acceptable. Excitation fluences should remain low enough so that cervical tissue is not vaporized and so that significant photo-bleaching does not occur. In arterial tissue, for example, significant photo-bleaching occurs above excitation fluences of about 80 $mJ/mm^2$.

The proximal ends of the collection fibers 104, 108–111 are preferably arranged in a circular array and imaged at the entrance slit of a polychromator 114 (Jarrell Ash, Monospec 18) coupled to an intensified 1024-diode array 116 controlled by a multi-channel analyzer 117 (Princeton Instruments, OMA). Long pass filters for 370 nm, 400 nm, and 470 nm wavelengths were used to block scattered excitation light at 337 nm, 380 nm, and 460 nm excitation, respectively. A 205 ns collection gate, synchronized to the leading edge of the laser pulse using a Pulser 118 (Princeton Instruments, PG200), effectively eliminated the effects of the colposcope's white light illumination during fluorescence measurements. Data acquisition and analysis were controlled by computer 119 in accordance with the fluorescence diagnostic method described below.

The system of FIG. 2 is an exemplary embodiment and should not be considered to limit the invention as claimed. It will be understood that spectroscopic apparatus other than that depicted in FIG. 2 may be used without departing from the scope of the invention.

Data Sets

The present invention can be implemented in several embodiments. All of the embodiments use a classification method based on neural networks, particularly radial basis function (RBF) and multi-layer perception (MLP) neural networks. The invention can be used on the following data sets:
(1) pre-processed full spectra intensity values;
(2) pre-processed reduced-parameter intensity values;
(3) principal component scores derived from pre-processed full spectra intensity values or from pre-processed reduced-parameter intensity values.

While the full excitation-emission spectra intensity values can be used as input to the neural networks of the present invention, the preferred embodiments use pre-processed reduced-parameter intensity values or principal component scores as input. In a first embodiment, a two-stage analysis is used. In a second embodiment, a single-stage analysis is used.

Derivation of Principal Component Scores

Principal component scores can be determined using a four-step method: (1) preprocessing of spectral data from each patient to account for inter-patient variation and intra-patient variation of spectra from a diagnostic category; (2) partitioning of the pre-processed spectral data from all patients into calibration and prediction sets; (3) dimension reduction of the pre-processed spectra in the calibration set using principal component analysis; (4) selection of the diagnostically most useful principal components using a two-sided unpaired Student's t-test. The steps for deriving principal component values are presented below in more detail.

(1) Preprocessing: The objective of preprocessing is to calibrate tissue spectra for inter-patient and intra-patient variation which might obscure differences in the spectra of different tissue types. In the preferred embodiment, four alternative methods of preprocessing can be used with the spectral data: 1) normalization; 2) mean scaling; 3) a combination of normalization and mean scaling; and 4) median scaling. However, other methods of calibrating tissue spectra can be applied.

Spectra were normalized by dividing the fluorescence intensity at each emission wavelength by the maximum fluorescence intensity of that sample. Normalizing a fluorescence spectrum removes absolute intensity information; methods developed from normalized fluorescence spectra rely on differences in spectral line shape information for diagnosis. If the contribution of the absolute intensity information is not significant, two advantages are realized by utilizing normalized spectra: 1) it is no longer necessary to calibrate for inter-patient variation of normal tissue fluorescence intensity; and 2) identification of a colposcopically normal reference site in each patient before spectroscopic analysis is no longer needed.

Mean scaling was performed by calculating the mean spectrum for a patient (using all spectra obtained from cervical sites in that patient) and subtracting the mean spectrum from each spectrum in that patient. Mean-scaling can be performed on both unnormalized (original) and normalized spectra. Mean-scaling does not require colposcopy to identify a reference normal site in each patient prior to spectroscopic analysis. However, unlike normalization, mean-scaling displays the differences in the fluorescence spectrum from a particular site with respect to the average spectrum from that patient. Therefore, this method can enhance differences in fluorescence spectra between tissue categories most effectively when spectra are acquired from approximately equal numbers of non-diseased and diseased sites from each patient.

Median scaling is performed by calculating the median spectrum for a patient (using all spectra obtained from cervical sites in that patient) and subtracting the median spectrum from each spectrum in that patient. Like mean scaling, median scaling can be performed on both unnormalized (original) and normalized spectra, and median scaling does not require colposcopy to identify a reference normal site in each patient prior to spectroscopic analysis. However, unlike mean scaling, median scaling does not require the acquisition of spectra from equal numbers of non-diseased and diseased sites from each patient.

(2) Calibration and Prediction Data Sets: The pre-processed spectral data were randomly assigned into either a calibration or prediction set. Neural networks were developed and optimized using the calibration set. The neural networks were then tested prospectively on the prediction data set.

(3) Principal Component Analysis: Dimension reduction is useful because fluorescence spectra at all three excitation wavelengths comprise a total of 160 excitation-emission wavelengths pairs at a 5 nm resolution for emission wavelengths. However, there is a significant cost penalty for using all 160 values. To alleviate this concern, a more cost-effective fluorescence imaging system is used, using component loadings calculated from principal component analysis (PCA). Accordingly, the number of required fluorescence excitation-emission wavelength pairs was reduced from 160 to 13 with a minimal drop in classification accuracy (however, more than 13 pairs can be used).

PCA is a linear model which transforms the original variables of a fluorescence emission spectrum into a smaller set of linear combinations of the original variables, called principal components, that account for most of the variance of the original data set. Principal component analysis is described in detail in W. R. Dillon, et al., *Multivariate Analysis: Methods and Applications,* John Wiley & Sons, 1984, pp. 23–52, which is incorporated by reference. While PCA may not provide direct insight to the morphologic and biochemical basis of tissue spectra, it provides a novel way of condensing all the spectral information into a few manageable components, with minimal information loss. Furthermore, each principal component can be easily related back to the original emission spectrum, thus providing insight into diagnostically useful emission variables.

Prior to PCA, a data matrix is created where each row of the matrix contains the pre-processed fluorescence spectrum of a sample and each column contains the pre-processed fluorescence intensity at each emission wavelength. A data matrix D (r×c), consisting of r rows (corresponding to r total samples from all patients in the training set) and c columns (corresponding to intensity at c emission wavelengths), can be written as:

$$D = \begin{pmatrix} D_{11} & D_{12} & \ldots & D_{1c} \\ D_{21} & D_{22} & \ldots & D_{2c} \\ & & & \\ D_{r1} & D_{r2} & \ldots & D_{rc} \end{pmatrix} \quad \text{Eq. (1)}$$

The first step in PCA is to calculate the covariance matrix, Z. First, each column of the pre-processed data matrix D is mean-scaled. The mean-scaled pre-processed data matrix, $D_m$ is then multiplied by its transpose and each element of the resulting square matrix is divided by (r−1), where r is the total number of samples. The equation for calculating Z is defined as:

$$Z = \frac{1}{r-1}(D'_m D_m) \quad \text{Eq. (2)}$$

The square covariance matrix, Z (c×c) is decomposed into its respective eigenvalues and eigenvectors. Because of experimental error, the total number of eigenvalues will always equal the total number of columns c in the data matrix D, assuming that c<r. The goal is to select n<c eigenvalues that can describe most of the variance of the original data matrix to within experimental error. The variance, V, accounted for by the first n eigenvalues, can be calculated as follows:

$$V = 100 \left( \frac{\sum_{j=1}^{n} \lambda_j}{\sum_{j=1}^{c} \lambda_j} \right) \quad \text{Eq. (3)}$$

The criterion used in this analysis was to retain the first n eigenvalues and corresponding eigenvectors that account for 99% of the variance in the original data set.

Next, the principal component score matrix can be calculated according to the following equation:

$$R = DC \quad \text{Eq. (4)}$$

where D (r×c) is the pre-processed data matrix and C (c×n) is a matrix whose columns contain the n eigenvectors which correspond to the first n eigenvalues. Each row of the score matrix R (r×c) corresponds to the principal component scores of a sample and each column corresponds to a principal component. The principal components are mutually orthogonal.

Finally, the component loading is calculated for each principal component. The component loading represents the correlation between the principal component and the variables of the original fluorescence emission spectrum. The component loading can be calculated as shown below:

$$CL_{ij} = \frac{C_{ij}}{\sqrt{S_{ii}}} \sqrt{\lambda_j} \quad \text{Eq. (5)}$$

where $CL_{ij}$ represents the correlation between the $i^{th}$ variable (pre-processed intensity at $i^{th}$ emission wavelength) and the $j^{th}$ principal component, $C_{ij}$ is the $i^{th}$ component of the $j^{th}$ eigenvector, $\lambda_j$ is the $j^{th}$ eigenvalue, and $S_{ii}$ is the variance of the $i^{th}$ variable.

In the preferred embodiment, principal component analysis was performed on each type of pre-processed data matrix, described above. Eigenvalues accounting for 99% of the variance in the original pre-processed data set were retained. The corresponding eigenvectors were then multiplied by the original data matrix to obtain the principal component score matrix R. Finally, the component loading of each principal component was calculated.

(4) Student s 1-test: Average values of principal component scores were calculated for each principal component obtained from the pre-processed data matrix. A one-sided unpaired Student's t-test was employed to determine the diagnostic contribution of each principal component. Such a test is disclosed in J. L. Devore, *Probability and Statistics for Engineering and the Sciences,* Brooks/Cole, 1992, and in R. E. Walpole et al., *Probability and Statistics for Engineers and Scientists,* Macmillan Publishing Co., 1978, Chapter 7, both of which are incorporated by reference. The hypothesis that the means of the principal component scores of two tissue categories are different were tested for 1) normal squamous epithelia and SILs, 2) columnar normal epithelia and SILs, and 3) inflammation and SILs. The t-test was extended a step further to determine if there were any statistically significant differences between the means of the principal component scores of high grade SILs and low grade SILs. Principal components for which the hypothesis stated above were true below about the 0.1 level of significance, and preferably below about the 0.05 level of significance, were retained for classification.

Pre-processed Full Spectra Intensity Values

As noted above, fluorescence spectra at all three excitation wavelengths comprise a total of 160 excitation-emission wavelengths pairs at a 5 nm resolution for emission wavelengths. While costlier to implement, the invention can use pre-processed full spectra intensity values as input to the neural network classifiers. In this case, steps (1) and (2) of the principal component scores derivation above are performed on the full spectra intensity values.

Pre-processed Reduced-Parameter Intensity Values

The component loadings at all three excitation wavelengths were evaluated to select fluorescence intensities at a minimum number of excitation-emission wavelength pairs to provide essentially the same classification accuracy as the full spectra and PCA scores. Use of these excitation-emission wavelength pairs greatly simplifies the data analysis. Table 2 sets forth the 15 preferred excitation-emission wavelength pairs (only two of the pairs in the second column differ from the first column). Some variance (e.g., −10 nm) from these values should give essentially the same results.

TABLE 2

| Feature for 1st Stage Analysis (normalized) $\lambda_{ex}, \lambda_{em}$ (nm) | Feature for 2nd Stage Analysis (normalized & mean-scaled) $\lambda_{ex}, \lambda_{em}$ (nm) |
|---|---|
| 337, 410 | 337, 410 |
| 337, 430 | 337, 430 |
| 337, 510 | 337, 510 |
| 337, 580 | 337, 580 |
| 380, 410 | 380, 410 |
| 380, 430 | 380, 430 |
| 380, 510 | 380, 510 |
| 380, 580 | 380, 580 |
| 380, 640 | 380, 600 |
| 460, 580 | 460, 580 |
| 460, 600 | 460, 600 |
| 460, 620 | 460, 620 |
| 460, 640 | 460, 660 |

Theoretical Basis for Radial Functions

Neural networks are a class of computational techniques that are loosely based on models of biological brain functioning. They are generally characterized by their adaptation of internal weights to an external input to "learn" the solution of a computational problem.

In accordance with the preferred embodiment of the invention, RBF neural networks are employed in the cervical pre-cancer diagnosis procedure. RBF neural networks employ "supervised learning." The goal of supervised learning is to estimate a function from example input-output pairs with little or no prior knowledge of the form of the function. The function is learned from the examples which a "teacher" supplies. The set of examples, or training set, contains elements which consist of paired values of the independent (input) variable and the dependent (output) variable. For example, in the functional relation:

$$y = f(x) \qquad \text{Eq. (6)}$$

the independent (input) variable is x (a vector), and the dependent (output) variable is y (a scalar). (Bold lower-case letters represent vectors and non-bold lower-case letters represent scalars, including scalar valued functions like f). The value of the variable y depends, through the function f, on each of the components of the vector variable:

$$R = DC \qquad \text{Eq. (7)}$$

The training set, in which there are p pairs (indexed by i running from 1 up to p), is represented by:

$$T = \{(x_i, \hat{y}_i)\}_{i=1}^{p} \qquad \text{Eq. (8)}$$

The ŷ symbol indicates an estimate or uncertain value. That is, the output values of the training set are usually assumed to be corrupted by noise. In other words, the correct value to pair with $x_i$, namely $y_i$, is unknown. The training set only specifies $\hat{y}_i$, which is equal to $y_i$ plus a small amount of unknown noise.

A linear model for a function f(x) takes the form:

$$f(x) = \sum_{j=1}^{m} w_j h_j(x) \qquad \text{Eq. (9)}$$

The model f is expressed as a linear combination of a set of m fixed functions (often called "basis" functions, by analogy with the concept of a vector being composed of a linear combination of basis vectors). The variable w is the coefficient of the linear combinations, and h is used for the basis functions; in neural network parlance, w and h represent weights and hidden units, respectively.

The flexibility off (i.e., its ability to fit many different functions) derives only from the freedom to choose different values for the weights. The basis functions and any parameters which they might contain are fixed. If this is not the case, if the basis functions can change during the learning process, then the model is nonlinear. Linear models are relatively simple to analyze mathematically. In particular, if supervised learning problems are solved by least squares, then it is possible to derive and solve a set of equations for the optimal weight values implied by the training set.

Any set of functions can be used as a basis set. Radial functions are a special class of functions. Their characteristic feature is that their response decreases (or increases) monotonically with distance from a central point. The center, the distance scale, and the precise shape of the radial function, are parameters of the model, which are all fixed if the model is linear.

A typical radial function is the Gaussian function, which, in the case of a scalar input, is:

$$h(x) = \exp\left(-\frac{(x-c)^2}{r^2}\right) \qquad \text{Eq. (10)}$$

Figure 3:
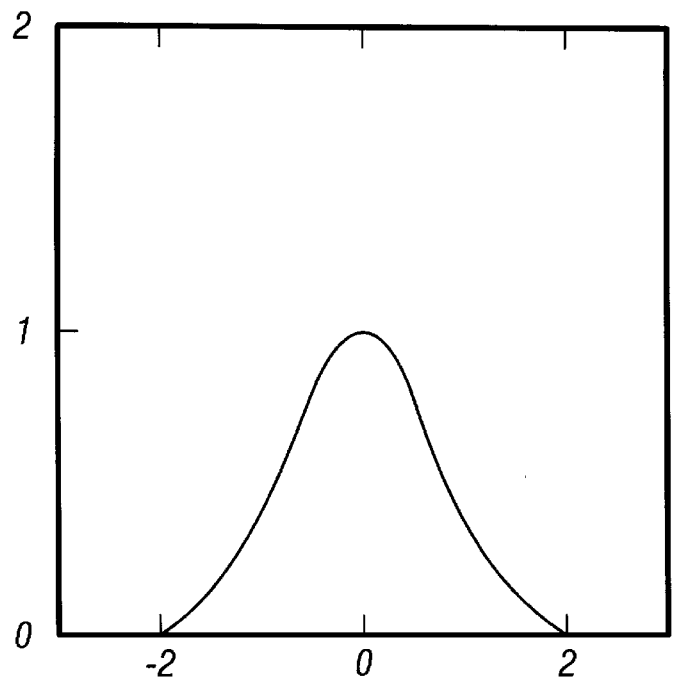
FIG. 3 is a graph depicting a radial basis function.
Figure 4:
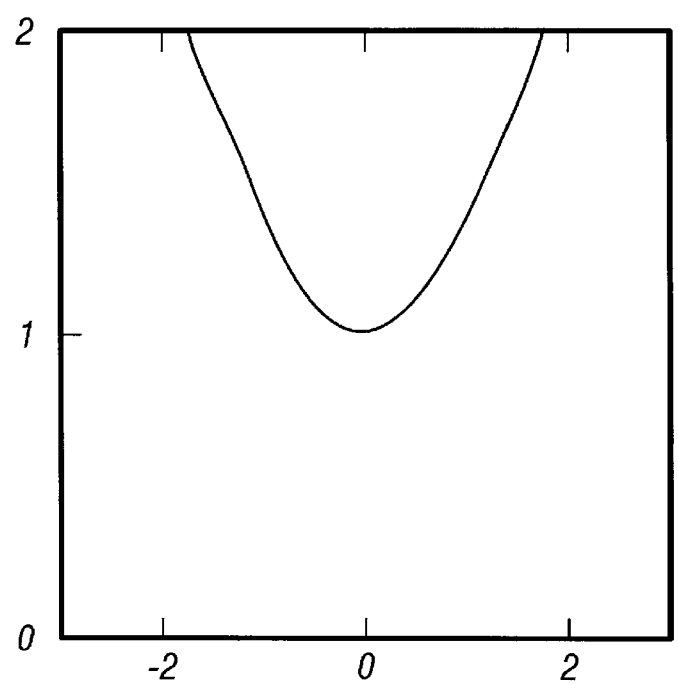
FIG. 4 is a graph depicting multiquadratic radial basis function.

The parameters of this function are its center c and its radius r. FIG. 3 illustrates a Gaussian radial function with center c=0 and radius r=1. A Gaussian radial function monotonically decreases with distance from the center. In contrast, a multiquadratic radial function monotonically increases with distance from the center, as shown in FIG. 4.

Radial Basis Function Neural Networks

Figure 5:
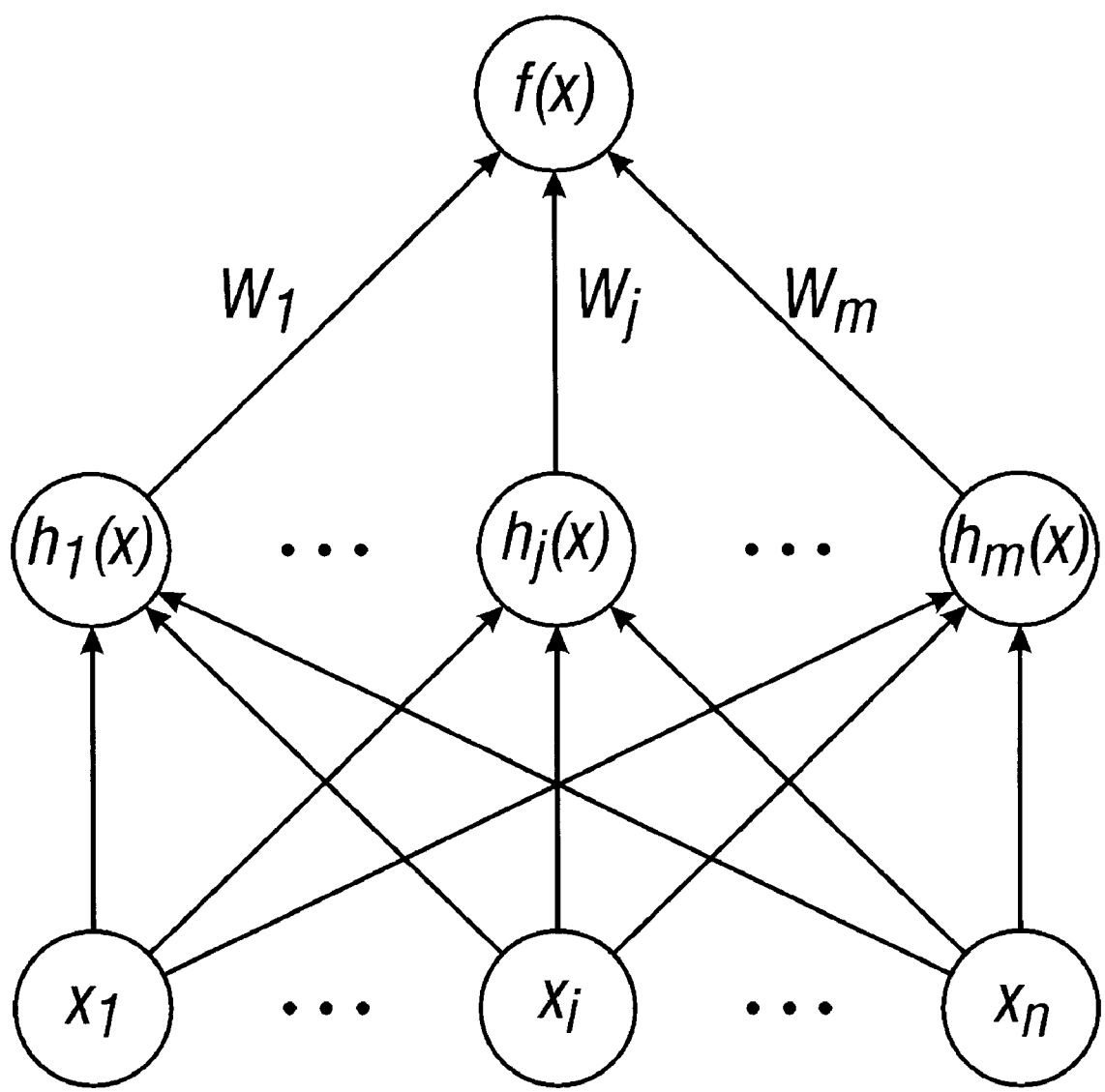
FIG. 5 is a diagram of a radial basis function neural network.

FIG. 5 is a diagram of a radial basis function neural network. Radial basis function neural networks have basis functions which are radial functions. In FIG. 5, each of n components of the input vector x feeds forward to m basis functions whose outputs are linearly combined into the network output j(x) with weights:

$$\{w_j\}_{j=1}^{m} \qquad \text{Eq. (11)}$$

When applied to supervised learning with linear models, the least-mean-squares principle leads to a particularly easy optimization problem. If the model for RBF output f(x) is Eq. 9 and the training set is $$\{(x_i, \hat{y}_i)\}_{i=1}^{p},$$

the least-mean-squares approach to reaching an optimal solution is to minimize the sum-squared-error:

$$S = \sum_{i=1}^{p} (\hat{y}_i - f(x_i))^2 \qquad \text{Eq. (12)}$$

with respect to the weights of the model. If a weight penalty term is added to the sum-squared-error, as is the case with ridge regression, then the following cost function is minimized:

$$C = \sum_{i=1}^{p}(\hat{y}_i - f(x_i))^2 + \sum_{j=1}^{m}\lambda_j w_j^2 \qquad \text{Eq. (13)}$$

where the $$\{\lambda_j\}_{j=1}^{m}$$

values are regularization parameters.

Minimization of the cost function leads to a set of m simultaneous linear equations in the m unknown weights. The linear equations can be written more conveniently as the matrix equation:

$$A\hat{w} = H^T \hat{y} \qquad \text{Eq. (14)}$$

where H, the design matrix, is:

$$H = \begin{bmatrix} h_1(x_1) & h_2(x_1) & \ldots & h_m(x_1) \\ h_1(x_2) & h_2(x_2) & \ldots & h_m(x_2) \\ \vdots & \vdots & \ddots & \vdots \\ h_1(x_p) & h_2(x_p) & \ldots & h_m(x_p) \end{bmatrix} \qquad \text{Eq. (15)}$$

and $A^{-1}$, the variance matrix, is:

$$A^{-1} = (H^T H + \Lambda)^{-1} \qquad \text{Eq. (16)}$$

The elements of the matrix A are all zero except for the regularization parameters along its diagonal, and $\hat{y} = [\hat{y}_1 \hat{y}_2 \ldots \hat{y}_p]^T$ is the vector of training set outputs. The solution is the so-called normal equation:

$$\hat{w} = A^{-1} H^T \hat{y}, \qquad \text{Eq. (17)}$$

where $\hat{w} = [\hat{w}_1 \hat{w}_2 \ldots \hat{w}_m]^T$ is the vector of weights which minimizes the cost function.

An alternative embodiment uses a gradient-descent procedure that represents a generalization of the least-mean-square algorithm. See, for example, Haykin, S., "*Neural Networks: A Comprehensive Foundation*", IEEE Press (1994). In this approach, the centers of the radial basis functions and all other free parameters of the network undergo a supervised learning process; in other words, the RBF network takes on its most generalized form. The first step in the development of a gradient-descent based learning procedure is to define the instantaneous value of the cost function:

$$\mathscr{E} = \frac{1}{2}\sum_{j=1}^{N} e_j^2 \qquad \text{Eq. (18)}$$

where N is the number of training examples used to undertake the learning process, and $e_j$ is the error signal, defined by:

$$e_j = d_j - F * (X_j) \qquad \text{Eq. (19)}$$

$$= d_j - \sum_{l=1}^{M} w_{lG}(\|x_l - t_l\|c_l)$$

The requirement is to find the free parameters $w_i$, $t_l$, and $\Sigma_l^{-1}$ (the latter being related to the norm-weighting matrix $C_j$) so as to minimize $\mathscr{E}$. The results of this minimization are summarized by the equations below. The term $e_j(n)$ is the error signal of output unit j at time n. The term $G'(*)$ is the first derivative of the Green's function $G(*)$ with respect to its argument.

Linear weights (output layer):

$$\frac{\partial \mathscr{E}(n)}{\partial w_i(n)} = \sum_{j=1}^{N} e_j(n) G(\|x_j - t_j(n)\|c_j) \qquad \text{Eq. (20)}$$

$$w_i(n+1) = w_i(n) - \eta_1 \frac{\partial \mathscr{E}(n)}{\partial w_i(n)}, \quad i = 1, 2, \ldots, M \qquad \text{Eq. (21)}$$

Positions of centers (hidden layer):

$$\frac{\partial \mathscr{E}(n)}{\partial t_i(n)} = 2w_i(n)\sum_{j=1}^{N} e_j(n) G'(\|x_j - t_j(n)\|c_j)\Sigma_i^{-1}[x_j - t_i(n)] \qquad \text{Eq. 22}$$

$$t_i(n+1) = t_i(n) - \eta_2 \frac{\partial \mathscr{E}(n)}{\partial t_i(n)}, \quad i = 1, 2, \ldots, M \qquad \text{Eq. (23)}$$

Spreads of centers (hidden layer):

$$\frac{\partial \mathscr{E}(n)}{\partial \Sigma_i^{-1}(n)} = -w_i(n)\sum_{j=1}^{N} e_j(n) G'(\|x_j - t_j(n)\|c_j) Q_{ji}(n) \qquad \text{Eq. (24)}$$

$$Q_{ji}(n) = [x_j - t_i(n)][x_j - t_i(n)]^T \qquad \text{Eq. (25)}$$

$$\Sigma_i^{-1}(n+1) = \Sigma_i^{-1}(n) - \eta_3 \frac{\partial \mathscr{E}(n)}{\partial \Sigma_i^{-1}(n)} \qquad \text{Eq. (26)}$$

Two-Stage Network Process

FIGS. 6–9 are flowcharts of the above-described fluorescence spectroscopy diagnostic methods of the invention. In practice, the flowcharts of FIGS. 6–10 are coded into appropriate form and are loaded into the program memory of a computer 119 (FIG. 2), which then controls the apparatus of FIG. 2 to cause the performance of the diagnostic method of the invention.

Figure 6:
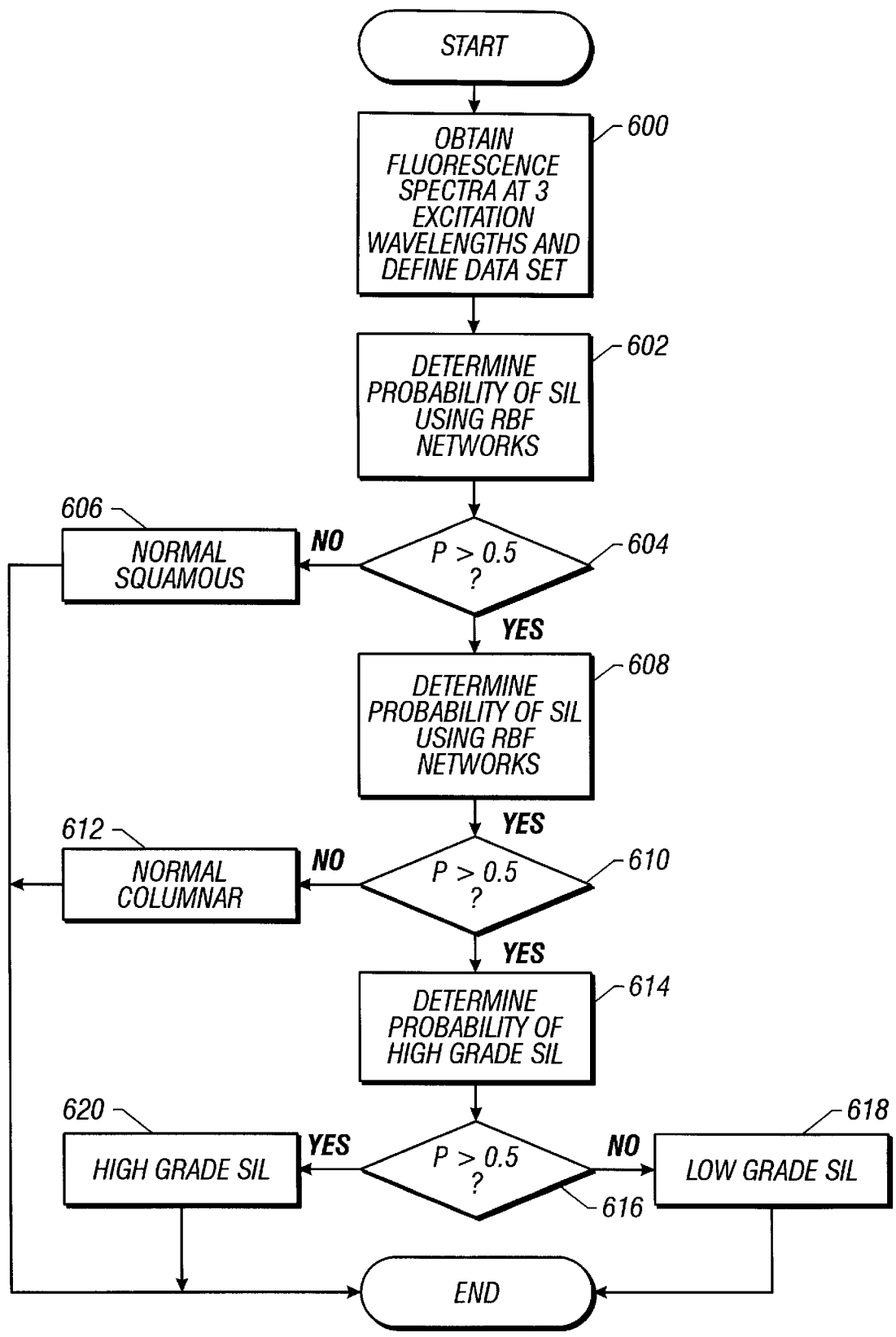
FIG. 6 is a flowchart of a two-stage fluorescence spectroscopy diagnostic method in accordance with the invention.

Referring first to FIG. 6, where a two-stage RBF method is shown, control begins in block 600 where fluorescence spectra are obtained from the patient at several excitation wavelengths (in this example, 337 nm, 380 nm, and 460 nm), and a data set is defined. For full spectra analysis, pre-processing is performed; for PCA data sets, the steps described above are performed; for reduced-parameter intensity values, pre-processing is performed on selected excitation-emission wavelength pairs.

Control then passes to block 602 where the probability of the tissue sample under consideration being SIL is calculated from the spectra obtained from the patient at either of two excitation wavelengths (in this example, 337 nm and 460 nm) using RBF classifiers.

Control then passes to decision block 604 where the probability of SIL calculated in block 602 is compared against a threshold of 0.5. If the probability is not greater than 0.5, control passes to block 606 where the tissue sample is diagnosed as normal squamous, and the routine ends. Otherwise, control passes to block 608 where the probability of the tissue containing SIL is calculated based upon the emission spectra obtained from another excitation wavelength (for example, at 380 nm). This second stage calculation is essentially the same as the method used in block 602.

Control then passes to decision block 610 where the probability of SIL calculated in block 608 is compared against a threshold of 0.5. If the probability calculated in block 608 is not greater than 0.5, control passes to block 612 where the tissue sample is diagnosed as normal columnar, and the routine ends. Otherwise, control passes to block 614 where the probability of SIL (high grade versus low grade) is calculated from the fluorescence emission spectra.

Control then passes to decision block 616 where the probability of high grade SIL calculated in block 614 is compared with a threshold of 0.5. If the probability calculated in block 614 is not greater than 0.5, low grade SIL is diagnosed (block 618), otherwise-high grade SIL is diagnosed (block 626). In some applications, a simple diagnosis of SIL (whether low grade or high grade) is sufficient, and the steps represented by blocks 614–620 can be omitted.

Figure 7:
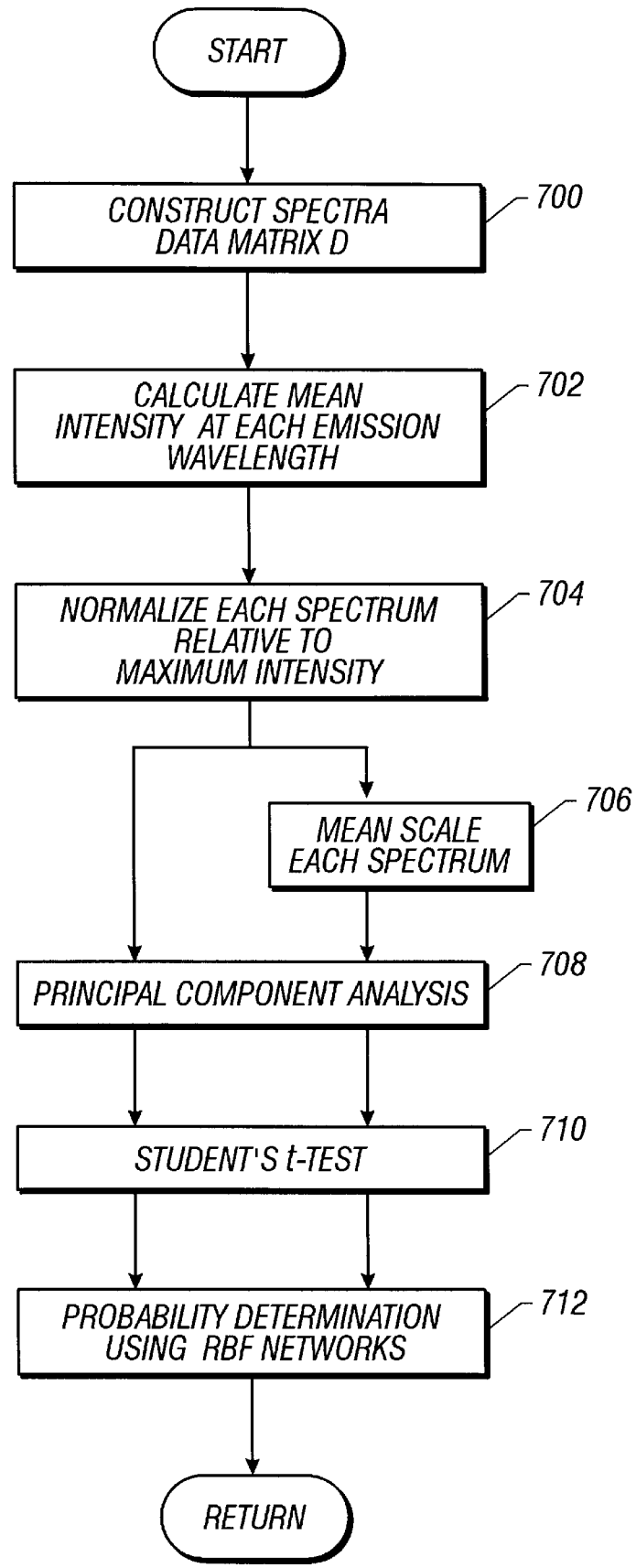
FIGS. 7 and 8 are flowcharts of a radial basis function neural network probability determination in accordance with the invention.

Referring now to FIG. 7, the data conditioning and classification probability determination of PCA-based fluorescence spectra (blocks 600, 602 and 608 in FIG. 6) is presented in more detail. It should be noted that while the processing of blocks 602 and 608 is identical, in the preferred embodiment, block 602 operates on normalized data, whereas block 608 operates on normalized, mean-scaled data. In either case, control begins in block 700, where the fluorescence spectra data matrix, D, is constructed, each row of which corresponds to a sample fluorescence spectrum taken from the patient. In the preferred embodiment, the spectra data comprises 160 excitation-emission pairs. Control then passes to block 702 where the mean intensity at each emission wavelength of the detected fluorescence spectra is calculated. In block 704, each spectrum of the data matrix is normalized relative to a maximum of each spectrum.

Figure 8:
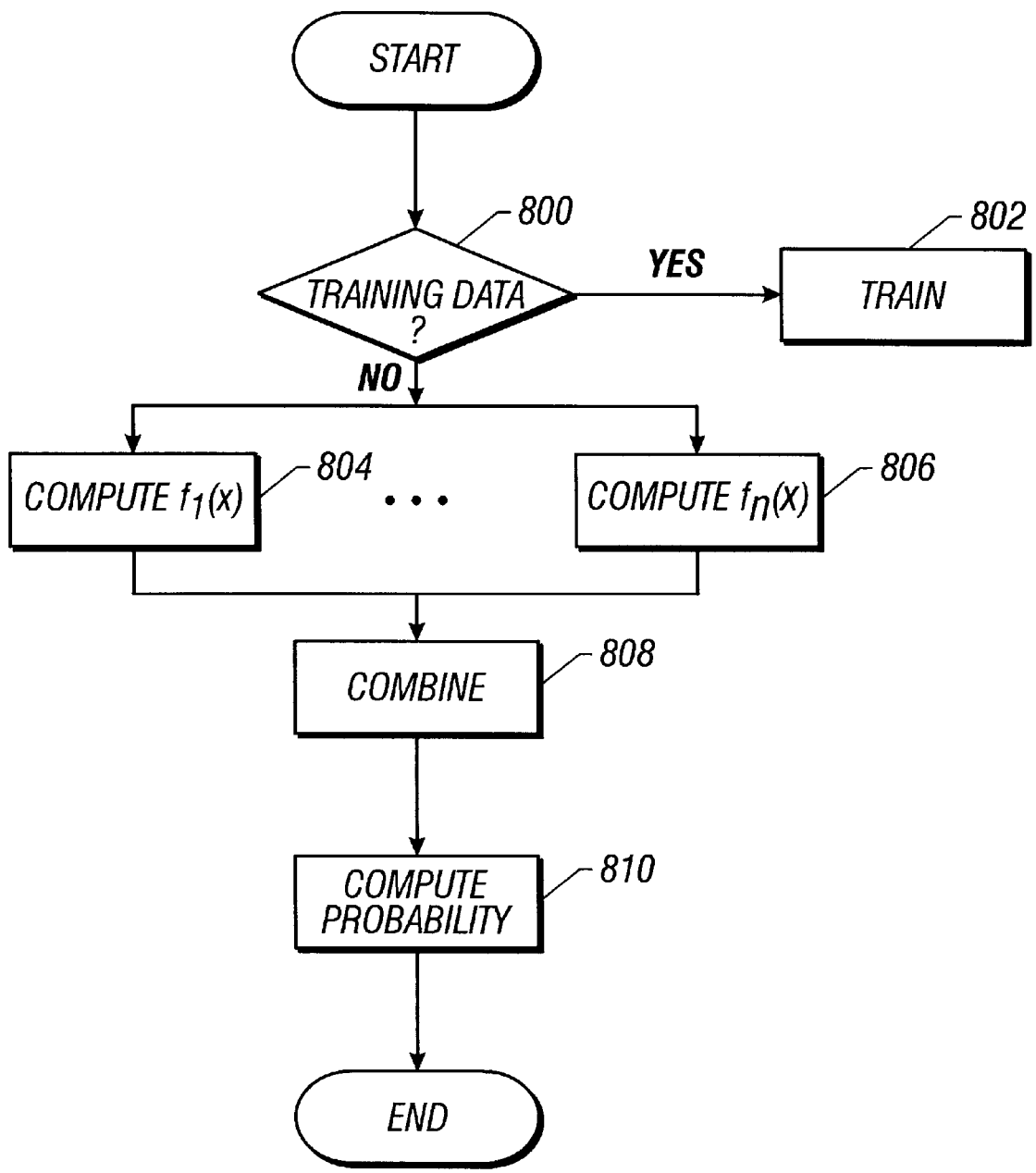

The data matrix D is then processed in two versions, one corresponding to the first stage of analysis (block 602), and the other corresponding to the second stage of analysis (block 608). In the first stage, control passes to block 708, where principal component analysis is conducted, as discussed above. During principal component analysis, the covariance matrix Z (Eq. 2), is calculated using a pre-processed data matrix, the rows of which comprise normalized spectra obtained from all patients in the training set. During training only, the result of block 708 is applied to block 710, where a Student's t-test is conducted which results in selection of only diagnostic principal components. Control then passes to block 712 where the results of block 710 are processed by an ensemble of RBF networks, as shown in FIG. 8, and combined.

During the second stage of processing, control passes from block 704 to block 706, in which each spectrum of the data matrix is mean-scaled relative to the mean calculated in block 702. When block 706 is being performed for the second stage of the two-stage process (as part of block 608), half of the kernels are fixed to patterns from the columnar normal (NC) class while the other half are initialized using a k-means clustering algorithm. Control then passes to block 708, where principal component analysis is conducted, as discussed above. During principal component analysis, the covariance matrix Z (Eq. 2), is calculated using a pre-processed data matrix, the rows of which comprise normalized, mean-scaled spectra obtained from all patients in the training set. Control then passes to block 712 (block 710 being performed only during training), where the results of block 708 are processed by an ensemble of RBF networks, as shown in FIG. 8, and combined.

For an embodiment using pre-processed reduced-parameter intensity values, the procedure in FIG. 7 is greatly simplified: after block 700, the desired excitation-emission wavelength pairs are selected and input to block 714.

For an embodiment using pre-processed full spectra intensity values, the procedure in FIG. 7 would omit blocks 708 and 710.

FIG. 8 is a flowchart of the above-described radial basis function probability determination, as performed in block 712 in FIG. 7. Control begins in decision block 800, where a determination is made whether the input data is training data or test data. If the input is training data, the RBF networks (such as those shown in FIG. 5) are trained in block 802, in conventional fashion. Each RBF network is trained with different initial points (weights) and a different sequence of the training examples. As a result, each RBF will generate a different result.

The number of training iterations for each RBF network will generally be a relatively large number, such as about 10,000. The optimum number of iterations can be determined experimentally by the number of iterations that it takes for an RBF network to reach an acceptable output, or a local or global minima.

The discrete class labels of the training set outputs are given numerical values by interpreting the $k^{th}$ class label as a probability of 1 that the example belongs to the class, and a probability of 0 that the example belongs to any other class. In general, the training output values are vectors of length equal to the number of classes containing a single 1 (and otherwise 0). For example, an RBF network will be trained to generate an output of 1 when the data is from a tissue sample that is abnormal and a 0 when the data represents normal tissue.

Once trained, control returns to block 800 until additional data is received. If the data received is not training data, control proceeds to blocks 804–806, representing an ensemble of RBF networks, each having a different RBF. For each RBF network, a design matrix H is set up in accordance with Equation 15 and the output of the RBF network is computed as shown in Equation 11, where $h_j$ corresponds to the design matrix H, and $w_j$ corresponds to the optimum weight matrix derived in Equation 17.

Control then passes to block 808 where the results of all of the RBF networks in the ensemble are combined in accordance with either the median combiner or averaging combiner. Block 810 then outputs the resultant probability of the input data being normal or abnormal.

An ensemble of RBF networks and a combiner were used because experimentation found that there were significant variations among different runs of individual RBF networks for both stages. Therefore, selecting the "best" classifier was not an ideal choice. First, the definition of "best" depends on the selection of the validation set, making it difficult to ascertain whether one network will outperform all others given a different test set, as the validation sets are small. Second, selecting only one classifier discards a large amount of potentially relevant information. In order to use all the available data, and to increase both the performance and the reliability of the methods, the outputs of the RBF networks were pooled before a classification decision was made.

The concept of combining classifier outputs has been widely reported. See, for example, the Hansen, et al. and Wolpert articles discussed below. In the preferred embodiment, either or both of two combiners were used: (1)

the median combiner, which belongs to the class order statistics combiners discussed in Turner, K. and Ghosh, J. (1995b), "Order statistics combiners for neural classifiers", Proceedings of the World Congress on Neural Networks, pp. I;3 1:34, Washington, D.C., INNS Press, and in Tumer, K. and Ghosh, J. (1995c), "Theoretical foundations of linear and order statistics combiners for neural pattern classifiers", Technical Report 95-02-98, The Computer and Vision Research Center, University of Texas, Austin; and (2) the well-known averaging combiner, which simply performs an arithmetic average of the corresponding outputs.

The performance of the RBF networks of the invention is preferably analyzed using a technique known as cross-validation. The basic idea is to use only a portion of the database in training the neural network and to use the rest of the database in assessing the capacity of the network to generalize. Once the performance of the network is assessed, the network can then be optimized by varying network characteristics and architecture. A residual error will typically remain even after optimizing all available network characteristics. Using an ensemble of networks, each of which have been trained on the same database, further reduces this error. Thus, a given input pattern is classified by obtaining a classification from each copy of the network and then using a consensus scheme to decide the collective classification result. A series of trial tunings of network parameters are preferably used to find an acceptable architecture in tuning. Instead of using just the best RBF network in the ensemble, the complete set of networks (or at least a screened subset) is used with an appropriate collective decision strategy.

Using the ensemble is desirable due to the basic fact that selection of the weights w is an optimization problem with many local minima. All global optimization methods in the face of many local minima yield "optimal" parameters (w) which differ greatly from one run of the algorithm to the next, i.e., which show a great deal of randomness stemming from different initial points ($w^0$) and sequencing of the training examples. This randomness tends to differentiate the errors of networks so that the networks will all make errors on different subsets of the input space. For additional discussion of the use of neural network ensembles, see L. Hansen, et al., "Neural Network Ensembles", *IEEE Transactions on Pattern Analysis and Machine Intelligence,* Vol. 12, No. 10, Oct. 1990, pages 993–1001, and D. Wolpert, "Stacked Generalization", *Neural Networks,* Vol. 5, 1992, pages 241–259, both of which are incorporated by reference.

In one implementation of the invention using two-stage RBF network classification, the kernels were initialized using a k-means clustering algorithm on the training set containing normal squamous (NS) tissue samples and SILs for the first stage. The RBF networks had 10 kernels, whose locations and spreads were adjusted during training. For the second stage, 10 kernels were selected, half of which were fixed to patterns from the columnar normal (NC) class, while the other half were initialized using a k-means algorithm. Neither the kernel locations nor their spreads were adjusted during training. This process was adopted to rectify the large discrepancy between the samples from each category (13 for columnar normal vs. 58 for SILs). For each stage, the training time was estimated by maximizing the performance on one validation set. Once the stopping time was established, 20 cases were run for each stage.

The ensemble results were based on pooling 20 different runs of RBF networks, initialized and trained as described above. This procedure was repeated 10 times to ascertain the reliability of the results and to obtain the standard deviations. For an application such as pre-cancer detection, the cost of a misclassification varies greatly from one class to another, as shown in FIG. 6. Erroneously labeling a healthy tissue as pre-cancerous can be corrected when further tests are performed. Labeling a pre-cancerous tissue as healthy, however, can lead to disastrous consequences. Therefore, for the first stage in the two-stage process, the cost of a misclassified SIL was increased until the sensitivity reached a satisfactory level. Results of using the two-stage RBF network process are discussed below.

Single-Stage Network Process

One drawback of the two-stage analysis is that it cannot concurrently distinguish SIL tissue from both normal squamous (NS) tissue and normal columnar (NC) tissue. Since the ultimate goal of these two stages is to separate SILs from normal tissue samples, any particular pattern has to be processed through both stages. For this reason, the two-stage process complicates the data gathering and decision-making processes. In order to simplify this decision process, a preferred embodiment of the invention uses a single-stage neural network analysis to classify the input data.

Essentially, the input for each of the stages of the two-stage process describe above are concurrently applied to an RBF network ensemble. Because the pre-processing for the first and second stages is different (i.e., normalization only vs. normalization plus mean-scaling), the input space in the preferred embodiment is 26-dimensional (ie., two sets of 13 data pairs). In one implementation, 10 kernels were initialized using a k-means algorithm on a trimmed version of the training set. The kernel locations and spreads were not adjusted during training to avoid kernel "migration" to a more heavily represented class. The cost of a misclassified SIL was set at 2.5 times the cost of a misclassified normal tissue sample, in order to provide a good sensitivity/specificity combination. The average and median combiner results were obtained by pooling 20 RBF networks.

Figure 9:
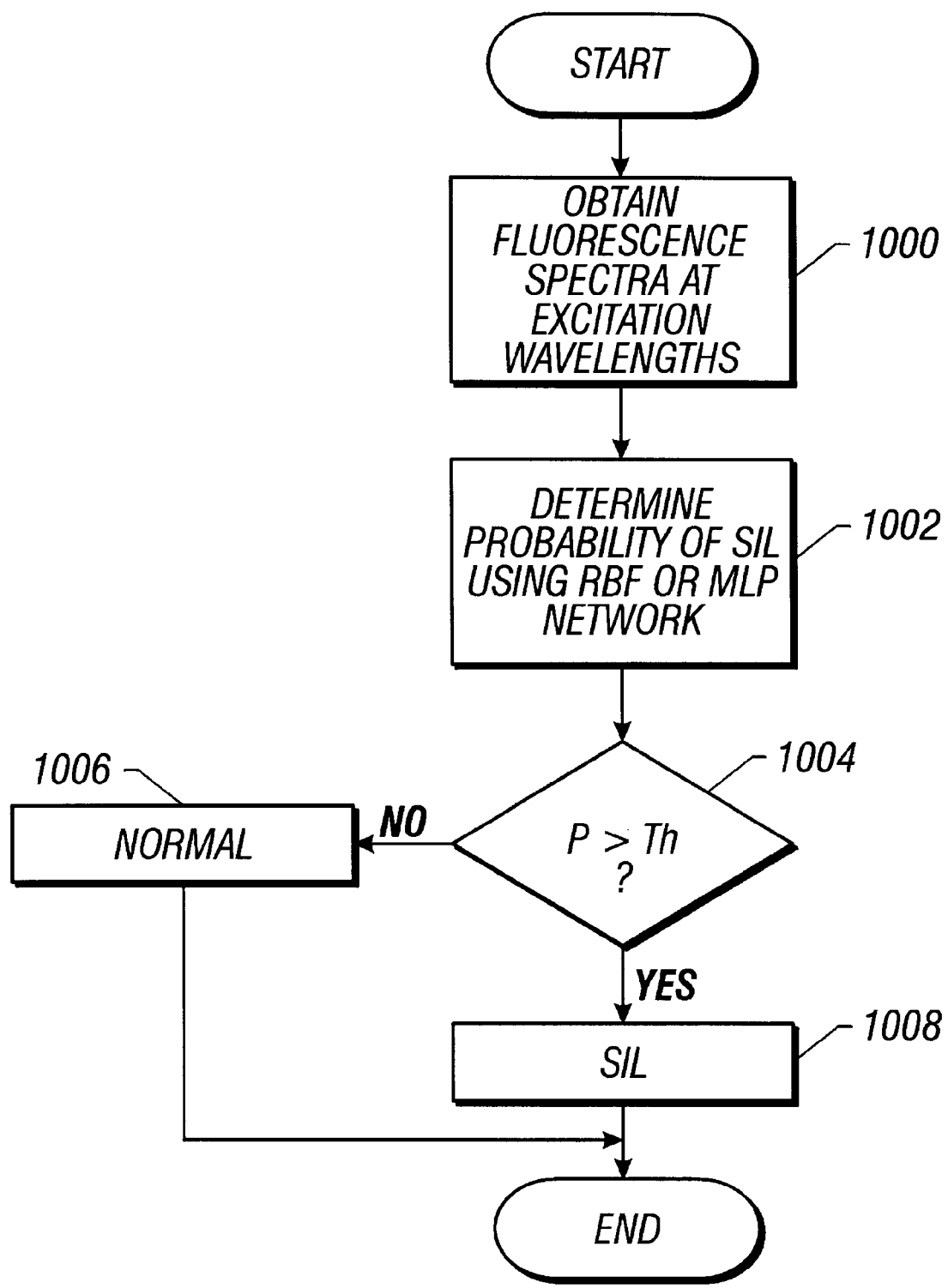
FIG. 9 is a flowchart of a one-stage fluorescence spectroscopy diagnostic method in accordance with the invention.

FIG. 9 is a block diagram for the single-stage fluorescence spectroscopy technique of the invention. In this process, in block 1000, the fluorescence spectrum at three excitation wavelengths are obtained. Control then proceeds to block 1002, where the probability of SIL is determined by an RBF ensemble. It should be noted that this procedure is similar to that shown in FIGS. 7 and 8, except that the input space is now larger because of the differences in the two combined steps discussed above.

Next, in decision block 1004, the probability is compared to a predetermined threshold, Th (e.g., 0.5). If the probability is less than the threshold, the process proceeds to decision block 1006 to determine whether the tissue is normal and, if so, the process determines in block 1008 that the tissue belongs to the SIL class. It will be appreciated that discrimination between high and low grade SIL can be added to the single-stage embodiment shown in FIG. 9 by simply adding steps corresponding to steps 614–620 shown in FIG. 6.

Results of using the single-stage RBF network process are discussed below.

MLP Network

Figure 10:
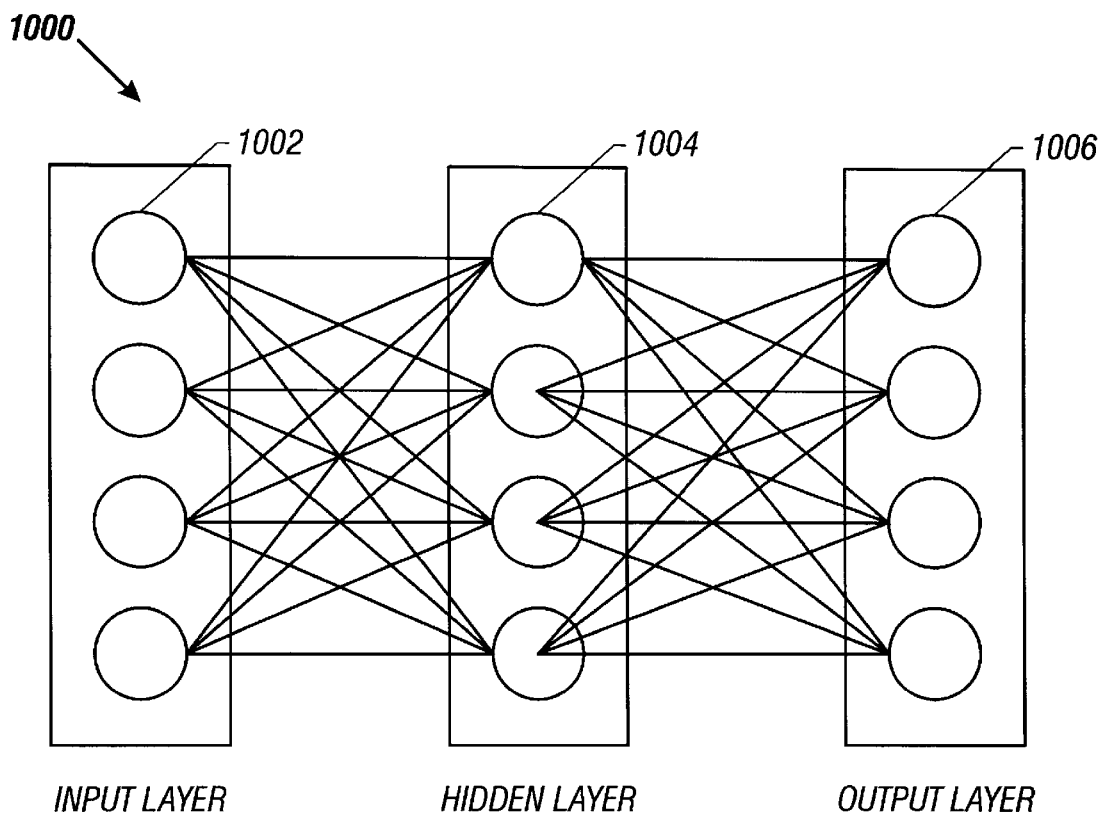
FIG. 10 is a block diagram of a multi-layer perceptron neural network trained by
back-propagation of error.

Although the preferred embodiments of the invention uses an RBF network, the invention can be implemented using a multi-layer perceptron (MLP) neural network 1000, such as is shown in block diagram form in FIG. 10. The MLP network 1000 includes an input layer comprising a plurality of input units 1002, a hidden layer comprising a plurality of hidden units 1004, and an output layer comprising a plurality of output units 1006 Each unit is a processing element or "neuron", coupled by connections having adjustable numeric weights or connection strengths by which earlier layers influence later ones to determine the network output. For further information on the architecture and training of MLP adaptive neural networks, see "*Progress in Supervised Neural Networks*" by Don Hush and Bill Horne, published in IEEE Signal Processing (January 1993).

Prior to using an MLP network to classify actual input data, a trainer is used to adjust the parameters of the neural network system 1000 using pre-characterized training data. The trainer monitors the neural network system's output and adjusts the parameters of the neural network system 1000 until a desired level of performance is achieved, in known fashion. Once an acceptable level of performance is achieved, the neural network system parameters are accepted and training stops. In the preferred embodiment of the present invention, training is done in accordance with the well-known back-propagation algorithm. This algorithm is described in an article entitled "*Back-Propagation, weight elimination and time series prediction*" by A. S. Weigend, D. E. Rumelhart, and B. A. Huberman, published in Proceedings Of The 1990 Connectionist Models Summer School, pp. 65–80 (1990), and in the Hush, et al article referenced above. If desired, a cross-validation system may be included, in known fashion.

In the preferred embodiment, an ensemble of MLP networks is used. The ensemble may be use with either a two-stage process or a single-stage process. Results of using an MLP network classifier are discussed below.

Results

Table 3 shows the sensitivity and specificity values for stage one of a two-stage classification process, based on MSA, MLP, and RBF ensembles. Table 4 presents sensitivity and specificity values for stage two for the same ensembles. For both stage one and stage two, the RBF-based ensembles provide higher specificity than the MSA method. For stage one, the MLP-based ensembles provide higher specificity than the MSA method. The median combiner provides results similar to those of the average combiner, except for stage two, where it provides better specificity.

The final results of both the two-stage and single-stage RBF process, and the results of the two-stage MSA process, are compared to the accuracy of Pap smear screening and colposcopy in expert hands in Table 5. A comparison of single-stage RBF process to the two-stage RBF process indicates that the single-stage process has similar specificities, but a moderate improvement in sensitivity relative to the two-stage process. Compared to the MSA, the single-stage RBF process has a similar specificity, but a substantially improved sensitivity. In addition to improved sensitivity, the single-stage RBF process simplifies the decision-making process compared to the two-stage process.

Figure 11:
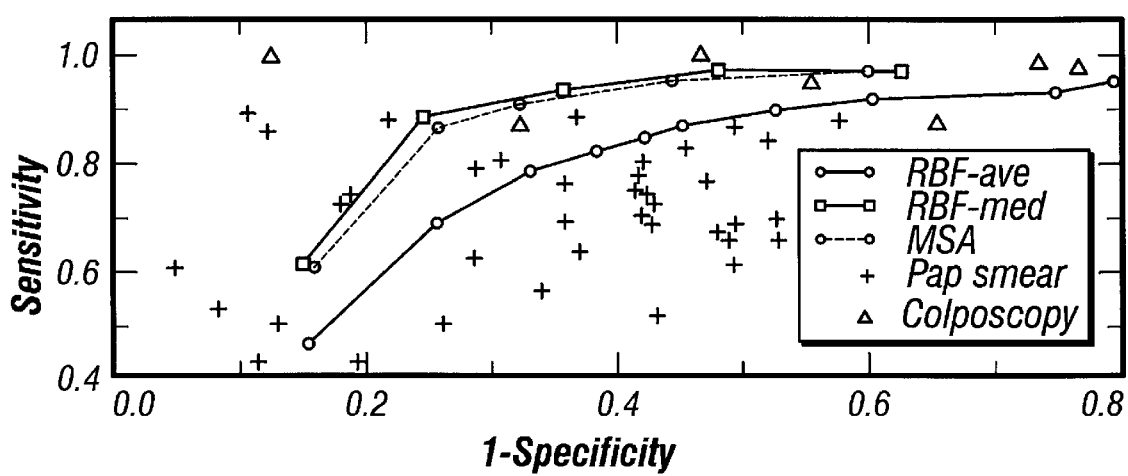
FIG. 11 is a graph of sensitivity versus specificity for various diagnostic procedures, including the embodiments of the invention.

A comparison between the single-stage RBF process and Pap smear screening indicates that the RBF algorithms have a nearly 30% improvement in sensitivity with no compromise in specificity. When compared to colposcopy in expert hands, the RBF ensemble processes maintain the sensitivity of expert colposcopists, while improving the specificity by almost 20%. FIG. 11 shows the trade-off between specificity and sensitivity for clinical methods, MSA, and RBF ensembles, obtained by changing the misclassification cost. The RBF ensembles provide better sensitivity and higher reliability than any other method for a given specificity value.

Figure 12:
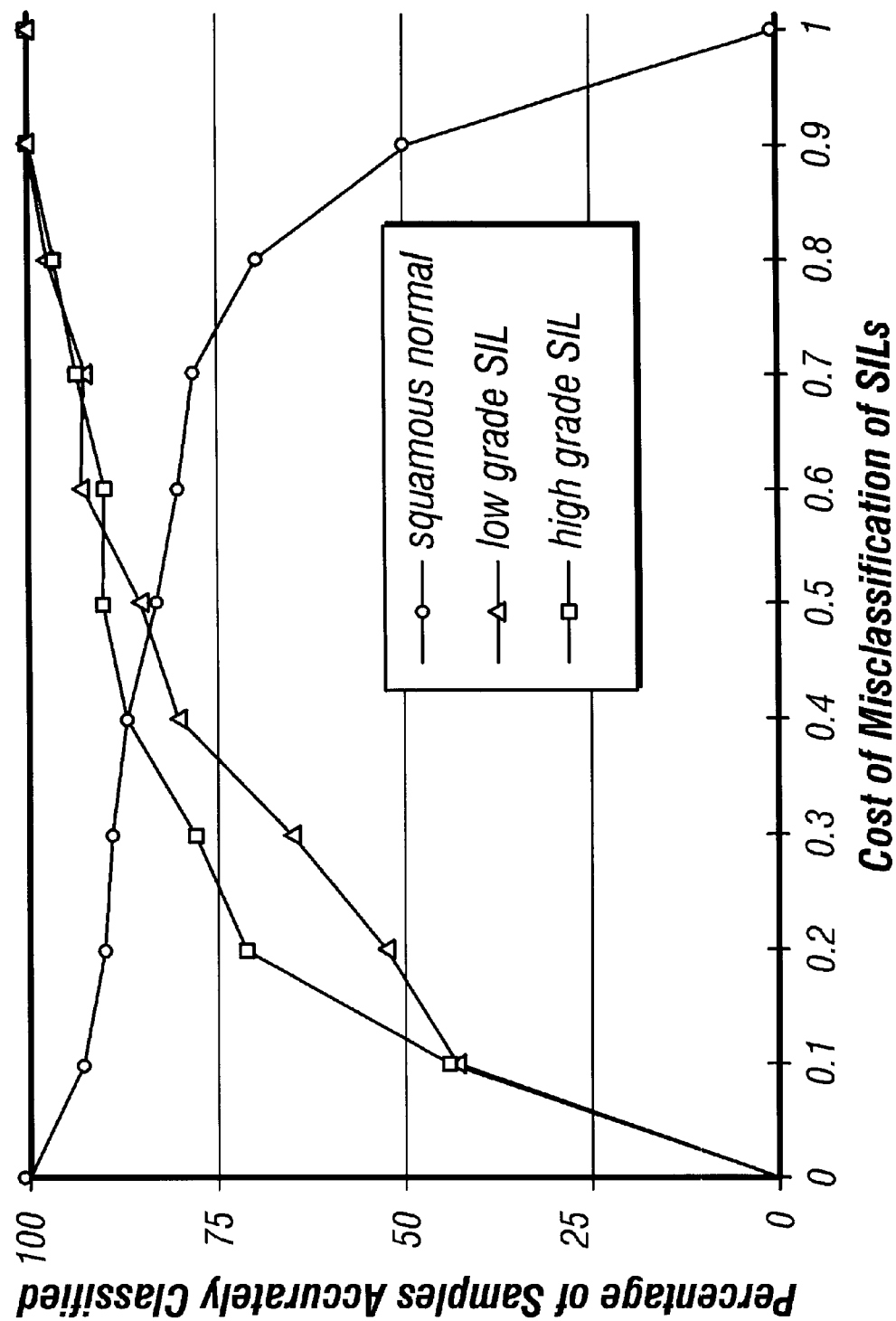
FIG. 12 is a graph depicting the performance of fluorescence diagnostic system versus the cost of misclassification in the training and classification process.

FIG. 12 shows the percentage of normal squamous tissues and SILs correctly classified versus cost of misclassification of SILs for the data from the calibration set in an MSA process. An increase in the SIL misclassification cost results in an increase in the proportion of correctly classified SILs and a decrease in the proportion of correctly classified normal squamous tissues. Varying the cost from 0.4 to 0.6 alters the classification accuracy of both SILs and normal tissues by less than 15%, indicating that a small change in the cost does not significantly alter the performance of the method. An optimal cost of misclassification would be about 0.6–0.7, as this correctly classifies almost 95% of SILs and 80% of normal squamous.

TABLE 3

Stage 1 of 2

| Algorithm | Specificity | Sensitivity |
| --- | --- | --- |
| MSA | 63% | 90% |
| MLP-ave | 61% ± 1% | 91% ± 0% |
| MLP-med | 61% ± 1% | 91% ± 0% |
| RBF-ave | 66% ± 1% | 91.5% ± 0.5% |
| RBF-med | 66% ± 1% | 91.5% ± 0.5% |

TABLE 4

Stage 2 of 2

| Algorithm | Specificity | Sensitivity |
| --- | --- | --- |
| MSA | 36% | 97% |
| MLP-ave | 50% ± 0% | 88% ± 0.7% |
| MLP-med | 50% ± 0% | 89% ± 2.5% |
| RBF-ave | 37% ± 5% | 97% ± 0% |
| RBF-med | 44% ± 7% | 97% ± 0% |

TABLE 5

Method Comparison

| Algorithm | Specificity | Sensitivity |
| --- | --- | --- |
| 2-stage MSA | 63% | 83% |
| 2-stage RBF-ave | 65% ± 2% | 87% ± 1% |
| 2-stage RBF-med | 67% ± 2% | 87% ± 1% |
| 1-stage RBF-ave | 67% ± 0.75% | 91% ± 1.5% |
| 1-stage RBF-med | 65.5% ± 0.5% | 91% ± 1% |
| Pap smear (human expert) | 68% ± 21% | 62% ± 23% |
| Colposcopy (human expert) | 48% ± 23% | 94% ± 6% |

Summary

Accordingly, the invention provides an apparatus and methods for spectroscopic detection of tissue abnormality, particularly precancerous cervical tissue, using neural networks to analyze in vivo fluorescence measurements. One embodiment of the invention is able to distinguish precancerous tissue from both normal squamous tissue (NS) and normal columnar (NC) tissue using a single-stage analysis. Using the inventive fluorescence diagnostic method, improved sensitivity and specificity were observed for differentiating squamous intraepithelial lesions (SILs) from all other tissues.

Computerized Implementation

The invention may be implemented in hardware or software, or a combination of both. However, preferably, the invention is implemented in computer programs executing on programmable computers each comprising at least one processor, at least one data storage system (including volatile and non-volatile memory and/or storage elements), at least one input device, and at least one output device. Program code is applied to input data to perform the functions described herein and generate output information. The output information is applied to one or more output devices, in known fashion.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage media or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

A number of embodiments of the invention have been described. Nevertheless, it will be understood that various modifications may be made without departing from the spirit and scope of the invention. For example, the teachings of the invention may be applied to other types of spectroscopic data generation modalities besides fluorescence spectroscopy, such as Raman spectroscopy, or to the diagnosis of conditions other than cervical pre-cancer. Accordingly, it is to be understood that the invention is not to be limited by the specific illustrated embodiment, but only by the scope of the appended claims.

What is claimed is:

1. An apparatus for detecting and classifying tissue abnormality at a tissue site, comprising:
   (a) at least one source of electromagnetic radiation of selected wavelengths that excite different fluorescence intensity spectra in normal and abnormal tissue;
   (b) a receiver sensitive to the fluorescence intensity spectra;
   (c) a tissue site probe coupled to each source and to the receiver; and
   (d) an ensemble of neural networks, coupled to the receiver, for calculating from the fluorescence intensity spectra a probability that the tissue site is normal or abnormal,
   wherein each neural network in such ensemble comprises a radial basis function (RBF) network for generating an associated probability estimate and further including a means for combining the probability estimates into a single probability.

2. An apparatus as in claim 1, wherein the means for combining utilizes a median class order statistical combiner.

3. An apparatus as in claim 1, wherein each neural network in such ensemble comprises:
   (a) a layer of input processing units receiving an input vector and producing an output;
   (b) a layer of hidden processing units each receiving one of the outputs from each of the input processing units and producing an output; and
   (c) an output unit receiving each hidden unit output multiplied by a weight, the output unit generating an output that is a function of its inputs.

4. An apparatus as in claim 1, wherein each neural network in such ensemble comprises a multilayer perceptron network for generating a probability estimate, and further including a means for combining the probability estimates into a single probability.

5. The apparatus as in claim 1, further including means for training the ensemble of neural networks using fluorescence intensity spectra from known normal and abnormal tissue.

6. An apparatus as in claim 5, wherein the training means adjusts the weight in an iterative process to produce a desired output in response to a given input, wherein the desired output comprises the probability.

7. An apparatus as in claim 1, wherein the fluorescence intensity spectra derives from abnormal cervical tissue, normal squamous cervical tissue, and normal columnar cervical tissue, wherein the probability is a single probability distinguishing abnormal tissue from both normal squamous and normal columnar tissue.

8. An apparatus as in claim 1, further including means for conducting a principle component analysis of the fluorescence intensity spectra.

9. An apparatus as in claim 8, further including means for normalizing the first fluorescence intensity spectra relative to respective maximum intensities thereof, prior to conducting the principle component analysis.

10. An apparatus as in claim 9, further including means for mean-scaling the first fluorescence intensity spectra as a function of a mean intensity thereof, prior to conducting the principle component analysis.

11. An apparatus as in claim 8, further including means for selecting component loadings calculated from the principal component analysis to reduce the number of excitation-emission wavelength pairs from the fluorescence intensity spectra required to train the ensemble of neural networks.

12. An apparatus as in claim 1, wherein at least one source of electromagnetic radiation comprises a laser operated to generate pulses at each wavelength having a power level, pulse duration, and repetition rate that excites the fluorescence intensity spectra in normal and abnormal tissue.

13. An apparatus as in claim 1, wherein the tissue is cervical tissue, and a probability of abnormal tissue indicates a cancerous or pre-cancerous condition.

14. A method for detecting and classifying tissue abnormality at a tissue site, comprising the steps of:
   (a) exciting different fluorescence intensity spectra in normal and abnormal tissue;
   (b) receiving the fluorescence intensity spectra; and
   (c) calculating from the fluorescence intensity spectra, using an ensemble of neural networks, a probability that the tissue site is normal or abnormal,
   wherein each neural network in such ensemble comprises a radial basis function (RBF) network for generating an associated probability estimate, and further including the step of combining the probability estimates into a single probability.

15. A method as in claim 14, wherein the step of combining utilizes a median class order statistical combiner.

16. A method as in claim 14, wherein each neural network in such ensemble comprises:
   (a) a layer of input processing units receiving an input vector and producing an output;
   (b) a layer of hidden processing units each receiving one of the outputs from each of the input processing units and producing an output; and
   (c) an output unit receiving each hidden unit output multiplied by a weight, the output unit generating an output that is a function of its inputs.

17. A method as in claim 14, each neural network in such ensemble comprises a multilayer perceptron network for generating a probability estimate, and further including the step of combining the probability estimates into a single probability.

18. The method as in claim 14, further including the step of training the ensemble of neural networks using fluorescence intensity spectra from known normal and abnormal tissue.

19. A method as in claim 18, further including the step of adjusting weights in each neural network in an iterative process to produce a desired output in response to a given input, wherein the desired output comprises the probability.

20. A method as in claim 14, wherein the fluorescence intensity spectra derives from abnormal cervical tissue, normal squamous cervical tissue, and normal columnar cervical tissue, wherein the probability is a single probability distinguishing abnormal tissue from both normal squamous and normal columnar tissue.

21. A method as in claim 14, further including the step of conducting a principle component analysis of the fluorescence intensity spectra.

22. A method as in claim 21, further including the step of normalizing the first fluorescence intensity spectra relative to respective maximum intensities thereof, prior to conducting the principle component analysis.

23. A method as in claim 22 further including the step of mean-scaling the first fluorescence intensity spectra as a function of a mean intensity thereof, prior to conducting the principle component analysis.

24. A method as in claim 21, further including the step of selecting component loadings calculated from the principal component analysis to reduce the number of excitation-emission wavelength pairs from the fluorescence intensity spectra required to train the ensemble of neural networks.

25. A method as in claim 14, wherein the different fluorescence intensity spectra are excited by a laser operated to generate electromagnetic radiation at selected wavelengths.

26. A method as in claim 14, wherein the tissue is cervical tissue, and a probability of abnormal tissue indicates a cancerous or pre-cancerous condition.

27. A method for in vivo analysis of cervical tissue, comprising the steps of:
(a) inserting an optical probe within a cervix, the probe having a light source and a light receptor;
(b) illuminating a selected area of the cervix with selected wavelengths of light from the light source;
(c) exciting fluorescence intensity spectra in both normal and abnormal tissue in the cervix with the light;
(d) receiving the fluorescence intensity spectra from the selected area through the light receptor;
(e) analyzing the received fluorescence intensity spectra, using an ensemble of neural networks, to determine a probability that the cervical tissue in the selected area is normal or abnormal
wherein each neural network in such ensemble comprises a radial basis function (RBF) network for generating an associated probability estimate, and further including the step of combining the probability estimates into a single probability.

28. A method as in claim 27, wherein each neural network in such ensemble comprises a multilayer perceptron network for generating a probability estimate, and further including the step of combining the probability estimates into a single probability.

29. A method for analyzing fluorescence intensity spectra from a tissue site in order to detect and classify tissue abnormality at the tissue site, comprising the step of:
(a) calculating from the fluorescence intensity spectra, using an ensemble of neural networks, a probability that the tissue site is normal or abnormal
wherein each neural network in such ensemble comprises a radial basis function (RBF) network for generating an associated probability estimate, and further including the step of combining the probability estimates into a single probability.

30. A method as in claim 29, wherein the step of combining utilizes a median class order statistical combiner.

31. A method as in claim 29, wherein each neural network in such ensemble comprises:
(a) a layer of input processing units receiving an input vector and producing an output;
(b) a layer of hidden processing units each receiving one of the outputs from each of the input processing units and producing an output; and
(c) an output unit receiving each hidden unit output multiplied by a weight, the output unit generating an output that is a function of its inputs.

32. A method as in claim 29, wherein each neural network in such ensemble comprises a multilayer perceptron network for generating a probability estimate, and further including the step of combining the probability estimates into a single probability.

33. The method as in claim 29, further including the step of training the ensemble of neural networks using fluorescence intensity spectra from known normal and abnormal tissue.

34. A method as in claim 33, further including the step of adjusting weights in each neural network in an iterative process to produce a desired output in response to a given input, wherein the desired output comprises the probability.

35. A method as in claim 29, wherein the fluorescence intensity spectra derives from abnormal cervical tissue, normal squamous cervical tissue, and normal columnar cervical tissue, wherein the probability is a single probability distinguishing abnormal tissue from both normal squamous and normal columnar tissue.

36. A method as in claim 29, further including the step of conducting a principle component analysis of the fluorescence intensity spectra.

37. A method as in claim 36, further including the step of normalizing the first fluorescence intensity spectra relative to respective maximum intensities thereof, prior to conducting the principle component analysis.

38. A method as in claim 36, further including the step of mean-scaling the first fluorescence intensity spectra as a function of a mean intensity thereof, prior to conducting the principle component analysis.

39. A method as in claim 36, further including the step of selecting component loadings calculated from the principal component analysis to reduce the number of excitation-emission wavelength pairs from the fluorescence intensity spectra required to train the ensemble of neural networks.

40. A method as in claim 29, wherein the fluorescence intensity spectra are excited by a laser operated to generate electromagnetic radiation at selected wavelengths.

41. A method as in claim 29, wherein the tissue is cervical tissue, and a probability of abnormal tissue indicates a cancerous or pre-cancerous condition.

42. A computer program, residing on a computer-readable medium, for detecting and classifying tissue abnormality at a tissue site using data in a computer derived from fluorescence intensity spectra of normal and abnormal tissue, the computer program comprising instructions for causing a computer to:
(a) pre-process the fluorescence intensity spectra data; and
(b) calculate a probability that the tissue site is normal or abnormal from the fluorescence intensity spectra data using an ensemble of neural networks,
wherein the computer program further comprises instructions for causing the computer to calculate the probability using an ensemble of radial basis function (RBF) networks, each generating an associated probability estimate, and to combine the probability estimates into a single probability.

43. A computer program as in claim 42, wherein the computer program further comprises instructions for causing the computer to train each RBF network using fluorescence intensity spectra from known normal and abnormal tissue.

44. A computer program as in claim 42, wherein the computer program further comprises instructions for causing the computer to conduct a principle component analysis of the fluorescence intensity spectra.

45. A computer program as in claim 44, further including instructions for causing the computer to select component loadings calculated from the principal component analysis to reduce the number of excitation-emission wavelength pairs from the fluorescence intensity spectra required to train the ensemble of neural networks.

46. A computer program as in claim 42, wherein the computer program further comprises instructions for causing the computer to calculate the probability using an ensemble of multilayer perceptron works, each generating an associated probability estimate and to combine the probability estimates into a single probability.

* * * * *